United States Patent [19]
Davis

[11] Patent Number: 6,066,088
[45] Date of Patent: May 23, 2000

[54] INTRAURETHRAL MAGNETIC VALVE

[75] Inventor: Phillip J. Davis, New York, N.Y.

[73] Assignee: Phillip Davis Inventions, Inc., New York, N.Y.

[21] Appl. No.: 09/114,354

[22] Filed: Jul. 13, 1998

[51] Int. Cl.$^7$ ....................................................... A61F 2/00
[52] U.S. Cl. ....................................... 600/29; 128/DIG. 25
[58] Field of Search ................ 600/29–30; 128/DIG. 25; 604/8, 9, 246, 247; 251/65, 337

[56] References Cited

U.S. PATENT DOCUMENTS

| | | |
|---|---|---|
| 3,731,670 | 5/1973 | Loe . |
| 3,812,841 | 5/1974 | Isaacson . |
| 5,004,454 | 4/1991 | Beyar et al. . |
| 5,030,199 | 7/1991 | Barwick et al. . |
| 5,040,002 | 8/1991 | Pollacek et al. . |
| 5,041,092 | 8/1991 | Barwick ..................... 600/29 |
| 5,140,999 | 8/1992 | Ardito . |
| 5,234,409 | 8/1993 | Goldberg et al. . |
| 5,366,506 | 11/1994 | Davis . |
| 5,624,374 | 4/1997 | Von Iderstein ............................ 600/29 |
| 5,713,877 | 2/1998 | Davis . |

FOREIGN PATENT DOCUMENTS

700668A1   3/1996   European Pat. Off. .

*Primary Examiner*—John P. Lacyk
*Attorney, Agent, or Firm*—Kenneth J. LuKacher

[57] ABSTRACT

An intraurethral magnetic valve for insertion in the human urethra of a person suffering from incontinence. The intraurethral magnetic valve includes a nonferromagnetic cylindrical housing, a valve seat assembly attached to one end of the housing, a spherical magnetic valve element disposed for universal movement in the housing, and a ring for retaining the valve element which is attached at the other end of the housing. The valve seat assembly has a nonferromagnetic valve seat sealing surface and ferromagnetic ring, each having concentric apertures for passage of fluid. The valve element is maintained in closed check position against the valve seat by attraction to the ferromagnetic ring, restricting the flow of fluid through the valve. An external magnet is used to impart magnetic torque and attraction to the valve element displacing it from the valve seat and opening the valve for fluid flow. On removal of the external magnet, the valve element returns to its closed check position on the valve seat. The intraurethral magnetic valve may further include a mechanism for relieving excessive fluid pressure at the end of the housing having the valve seat assembly, in which the valve seat assembly is axially slidable within the housing, rather than being attached to the housing. The mechanism has a spring disposed in the housing on the side of the valve seat assembly opposite the valve element, between another retaining ring and the valve seat assembly. The spring pushes the valve seat assembly against an annular flange attached to the housing. Under normal conditions, the valve seat assembly engages the annular flange. During excessive hydrostatic pressure, the pressure against the valve element and valve seat assembly compresses the spring to disengage the seat assembly from the annular flange and permit slow release of fluid through a passageway around the valve seat assembly until the excessive pressure is reduced.

33 Claims, 4 Drawing Sheets

INTRAURETHRAL MAGNETIC VALVE

FIELD OF THE INVENTION

The present invention relates to intraurethral valves that are used to provide a valving means for individuals suffering from an inability to control their bladder functions by substituting a magnetic actuated valve to control the flow of urine, and relates particularly to, an improved intraurethral magnetic valve with a spherical magnetic valve check which controls the flow of urine through the urethra by the applying and removing of an external magnetic force.

BACKGROUND OF THE INVENTION

Prior art intraurethral magnetic valves have relied on a wide variety of different magnetic valve configurations that attempt to control the fluid flow from the bladder. Examples of same can be defined and divided into three basic designs. The first design group is characterized by ferromagnetic spheres or slugs which seal an aperture by attraction to one or more fixedly located permanent magnets within a valve housing or are resiliently held in closed position by a spring, and are drawn or tilted away from the aperture by a strong permanent magnet or electromagnetic field induced by a hand-held magnet located outside the valve housing, see for example, U.S. Pat. Nos. 3,731,670, 5,004,454 and 5,140,999.

The second design group is characterized by permanent magnets bonded to nonmagnetic valve checks which are drawn to seal an aperture by attraction to a ferromagnetic element comprising all or part of an apertured valve seat or are resiliently held in closed position against the valve seat by a spring. These checks are drawn in a straight linear motion away from the apertured valve seat by a hand-held magnet outside the valve housing, see for example, U.S. Pat. No. 3,812,841.

The third design is characterized by a valve check containing a permanent cylindrical magnet and sealing in an arbitrary position against a planar valve seat of ferromagnetic material. This check is tilted off the valve seat by magnetic torque induced between the poles of an external hand-held switching magnet and the internal check magnet, see for example, U.S. Pat. No. 5,366,506, issued to the present inventor.

In U.S. Pat. No. 3,731,670, a corporeal fluid control using binary magnetic duct valve is disclosed wherein a mounting tube has two spaced magnets with a steel ball valve element therebetween. The ball valve element is selectively attracted to each of the magnets defining an open or closed state depending on which magnet the ball is engaged. The ball is reciprocated within the structure by an external magnetic force.

U.S. Pat. No. 5,004,454, is directed to an intraurethral magnetic valve. A valve element of a ferromagnetic material is held in sealing relation against a valve seat by a spring associated therewith. The valve is opened by imposing a magnetic force on the valve element drawing same away from the seat and stretching the spring.

U.S. Pat. No. 5,140,999, is directed to an implantable valve structure in which the valve element extends well within the bladder for increased lateral operational movement. The valve element has a compression spring engaging same in a closed or checked position. Upon inducement of an outside magnetic force the magnetizable member on the free end of the valve element within the bladder is displaced to the side moving the respective valve element off its valve seat opening the valve. No accommodation is made for bladder neck movements or changes in bladder inflation which may cause unwanted movements of the free end of the valve element.

The devices defined by the first group of prior art valves suffer from an intrinsic difficulty in balancing the magnetic force needed for adequate sealing with the need for reasonable operational range of the activation magnet.

Since magnetic forces are highly nonlinear, decreasing very rapidly with distance from the magnetic poles; when a ferromagnetic ball or slug is held against an apertured valve seat by a permanent magnet element, the respective switching magnet must be either very large or very close to induced the required force. The slug checks that are drawn to the side of the housing encounter high sidewall friction forces which are induced increasingly as the angle between the housing center line and the line of approach of the switching magnet increases.

In U.S. Pat. No. 3,812,841, a urethra magnetic valve structure can be seen in which a valve element is positioned on a movable magnetic core cylinder. The valve element is held in closed position by an attached spring. Inducing a high electromagnetic force from outside the body will move the magnetic core cylinder and valve element attached thereto opening the valve.

In U.S. Pat. No. 3,812,841, the valve check movement is constrained by the housing to a straight line which necessitates that unless the switching magnet approaches with its axis directly aligned on the center line the force will draw the check against the sidewall imparting torque induced friction decreasing the effectiveness and movement of the check with the valve housing.

The valve assembly in U.S. Pat. No. 5,366,506 overcomes the drawbacks of small working distance and sidewall friction associated with devices of the first and second design groups, but can exhibit high fluid drag and low fluid flow rates in a valve-open position due to the limited clearance between the valve check, containing a cylindrical magnet, and the sidewalls of the valve assembly's housing. Another embodiment of the valve assembly in U.S. Pat. No. 5,366,506 provides for a magnetic valve check hingedly attached to the housing of the valve assembly which can provide higher fluid flow rates in a valve-open position.

The present invention is directed to a magnetic valve providing an enhanced fluid flow rate therethrough in a construction which reduces the ratio between fluid drag and overall valve diameter. The magnetic valve includes a spherical magnet valve element which sealingly engages a nonferromagnetic valve seat by attraction to a ferromagnetic ring. The valve seat and the ferromagnetic ring comprise a valve seat assembly which is sealingly attached to an inner bore of a cylindrical nonmagnetic valve housing. Under an initial weak action of an approaching hand-held switching magnet, the valve element rotates in the valve seat, causing renal calculus and mucous deposits to be wiped off the valve element by the valve seat. Under stronger action of magnetic attraction induced by closer proximity of the switching magnet to the magnetic valve element, the valve element moves from the valve seat and thereby opens a valve lumen to fluid flow therethrough.

The magnetic valve of the present invention may further include a mechanism for relieving excessive fluid pressure, in which the valve seat assembly is slidable in an axial direction in the housing instead of being attached to the housing, and resiliently held by a compression spring in sealing engagement with an annular flange which is sealingly attached to the inner bore of the valve housing. The spring is constructed to define a condition of high fluid pressure relief. Under a condition of high fluid pressure, the valve element and the valve seat assemblies are displaced together in an axial direction within the housing so as to further compress the spring and thereby to permit slow release of fluid through a passageway around the valve seat assembly so as to reduce the high pressure condition. The provision of high pressure relief is particularly important in addressing a common and medically dangerous problem of high intravesical pressure caused in spinal cord injury patients by uncontrolled detrusor muscle contractions. Under normal conditions, the valve assembly is in sealing engagement with the annular flange, enabling the valve element and valve assembly to function responsive to the switching magnet, as described above.

SUMMARY OF THE INVENTION

It is the principal object of the present invention to provide an improved intraurethral magnetic valve which increases urine flow rate over prior art intraurethral magnetic valves.

It is another object of the present invention to provide an improved intraurethral magnetic valve which enables removal of deposits which can build up in the valve.

It is a further object of the present invention to provide an improved intraurethral magnetic valve which can include a high pressure relief mechanism when excess hydrostatic pressure occurs in the bladder.

Briefly described, the intraurethral magnetic valve of the present invention includes a nonferromagnetic cylindrical housing, a valve seat assembly sealing attached to one end of the housing, a spherical magnetic valve element disposed for universal movement in the housing, and a ring for retaining the valve element attached at the other end of the housing. The valve seat assembly has a nonferromagnetic valve seat sealing surface and ferromagnetic ring, each having concentric apertures for passage of fluid. The valve element is maintained in closed check position against the valve seat by attraction to the ferromagnetic ring, restricting the flow of fluid through the valve. An external switching magnet provides a magnetic force to impart magnetic torque and attraction to the valve element displacing the valve element from the valve seat and opening the valve for fluid flow. Displacement of the valve element in the housing is limited by the retaining ring. The magnetic attraction between the valve element and ferromagnetic ring is sufficient to close the valve on removal of the external switching magnet.

The magnetic valve operates in the urethra responsive to the switching magnet to control the flow of urine in a person unable to control their bladder function. The magnetic valve may also be reversed in the urethra to function as a high pressure relief valve for a man wearing a urine collection device who may be unable to operate the switching magnet.

The intraurethral magnetic valve may further include a mechanism for relieving excessive fluid pressure at the end of the housing having the valve seat assembly, in which the valve seat assembly is axially slidable within the housing, rather than being attached to the housing. The mechanism has a compression spring disposed in the housing on the side of the valve seat assembly opposite the valve element, between another retaining ring and the valve seat assembly. The spring pushes the valve seat assembly against an annular flange attached to the housing. Under normal conditions, the valve seat assembly sealingly engages the annular flange. However, during excessive hydrostatic pressure, the pressure against the valve element and valve seat assembly further compresses the spring to disengage the seat assembly from the annular flange and permit slow release of fluid through a passageway around the valve seat assembly until the excessive pressure is reduced. The valve element is sized to pass through the annular flange when the valve seat assembly is displaced. The magnetic valve thus can release small quantities of urine caused by uncontrolled bladder detrusor contractions, or pressure spikes due to, for example, coughs or sneezes.

BRIEF DESCRIPTION OF THE DRAWINGS

The foregoing objects, features and advantages of the invention will become more apparent from a reading of the following description in connection with the accompanying drawings in which.

DETAILED DESCRIPTION OF THE INVENTION

Figure 1:
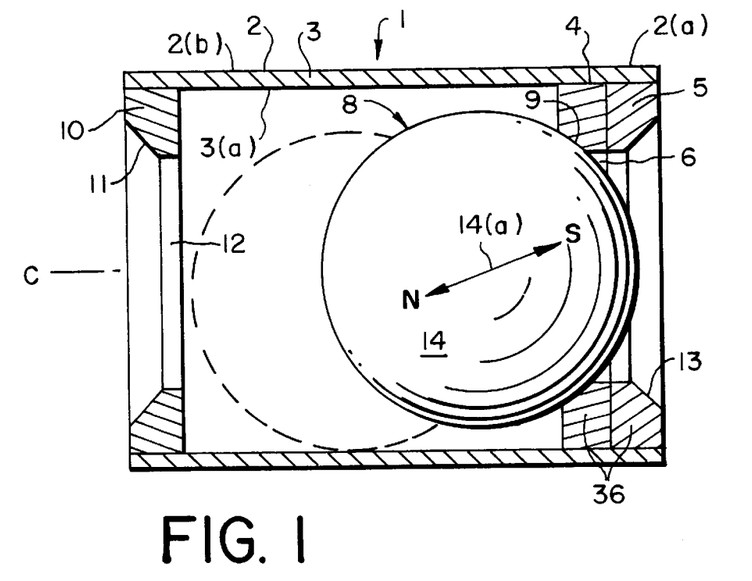
FIG. 1 is a sectional view taken through the intraurethral magnetic valve in accordance with the present invention.

Referring to FIG. 1, a valve assembly 1 comprises a cylindrical nonmagnetic valve housing 2 having a continuous sidewall 3. A valve seat assembly 36 is sealingly attached to an inner bore 3($a$) of the housing at one end 2($a$) of the housing. The valve seat assembly 36 comprises a nonferromagnetic valve seat 4 and a ferromagnetic attractive ring 5 of high magnetic permeability. Valve seat 4 has a cylindrical aperture 6 concentric with housing 2, and this aperture extends through ring 5, thereby providing valve seat assembly 36 with a cylindrical aperture.

A valve element 8 comprises a spherical permanent magnet 14 which is coated or plated with a biocompatible material. The valve element 8 is disposed for universal movement in the housing 2, but is normally attracted to the ring 5, causing it to occlude the cylindrical aperture 6 of the valve seat 4 by continuous contact with a conical, spherical, or generally concave face 9 which extends axially outward from cylindrical aperture 6. In other words, the spherical valve element 8 is normally in a valve-closed (close check) position against the valve seat 4. The face 9, i.e., the sealing surface of the valve seat 4, is spaced axially from the ferromagnetic ring to control the attractive force between the valve element 8 and the ring 5 and as such, the ring 5 and valve element 8 are in a noncontact relationship. Preferably, face 9 is spherical such that it matches the spherical exterior of valve element 8 when in a valve-closed position against the valve seat 4, thereby promoting a sealing surface to the valve element.

A nonmagnetic retaining ring 10 is sealingly attached to the inner bore 3($a$) of the housing 2 at the end 2($b$) of the housing. The retaining ring 10 has a conical face 11 which extends axially outward from a cylindrical aperture 12 concentric with the housing 2. Also, ring 5 has a conical face 13 which extends axially outward from the cylindrical aperture 6. The conical face 11 of the retaining ring 10, and the conical face 13 of ring 5 reduce fluid drag at respective cylindrical apertures 12 and 6. The retaining ring 10 prevents escape of the valve element 8 when the valve is in an open position and restricts axial displacement of the magnetic valve element 8, so that from all possible displacement positions sufficient magnetic attractive force exists between the valve element and the ferromagnetic ring 5 to return the valve element to sealing engagement with the valve seat 4.

Valve housing 2, valve seat 4, and retaining ring 10 are made of nonmagnetic biocompatible material, and the ferromagnetic ring 5 is coated or plated with a biocompatible material (not shown).

The spherical magnet 14 of the valve element 8 has a high residual flux density and high coercive force to achieve long term durability and to maintain an ability to sealingly engage the face 9 of the valve seat. The magnet 14 is magnetized as a dipole through an arbitrary center line, such as shown, for example, by N (north) and S (south) of center line 14(a).

In FIG. 1, the valve assembly 1 is shown in the valve-closed position. A valve-open position is schematically indicated by the dashed outline of the valve element 8 to depict the free range of travel of the valve element 8 within the housing 2 during operation of the valve, and thus to provide an indication of the relative clearance for fluid flow surrounding the valve element 8 within the housing 2 when the valve is open.

Figure 2:
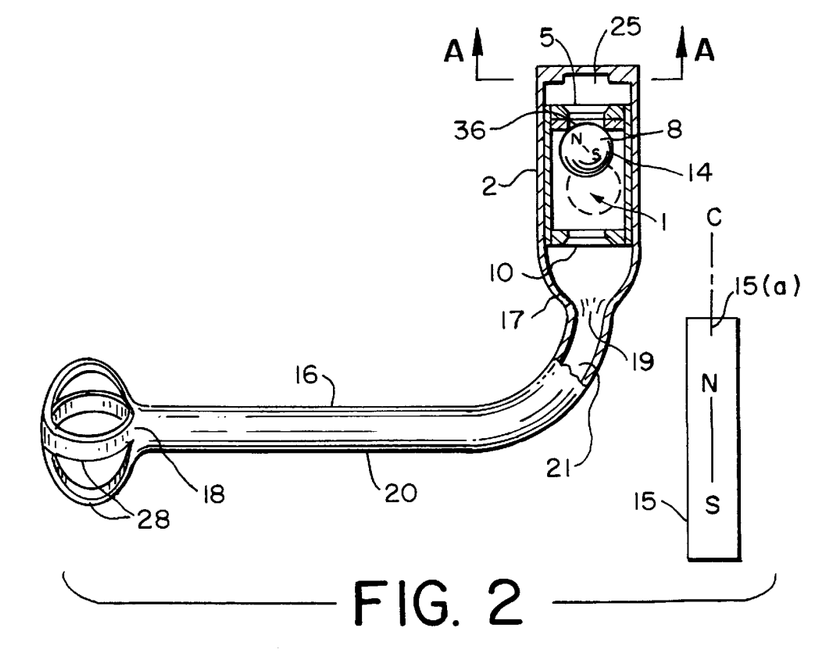
FIG. 2 is a side schematic plan view of the intraurethral magnetic valve of FIG. 1 shown in a catheter assembly.

Referring now to FIG. 2, an intraprostatic stent catheter assembly 16 is shown containing the valve assembly 1. The valve assembly is normally placed in a bulge 17 at the distal end of the intraprostatic stent catheter 16 and oriented so that the valve opens against pressure as shown schematically by dashed outline in FIG. 2. The stent 16 comprises a flexible tube 20 of a biocompatible material having lumen 21, an inlet port 18 and an outlet port 19, retaining loops (or rings) 28 at the proximal end of the stent, and bulge 17 containing valve assembly 1 and having a distal end outlet port 25.

A valve-open position occurs upon activation of the valve element 8 by a hand-held external switching magnet 15. The switching magnet 15 is of a generally bar configuration which, in the example shown here, has been magnetized along its longitudinal center line axis 15(a). When the switching magnet 15 approaches the valve element 8, magnetic torque induced by a misalignment of their respective magnetic center lines causes the valve element 8 to rotate on the valve seat assembly 36 (i.e., on the valve seat face 9 shown in FIG. 1), causing renal calculus and mucous deposits to be wiped off the surface of the valve element 8 until unlike poles of the magnets 14 and 15 are drawn together. When there is a net force of torque and attraction between the valve element 8 and the switching magnet 15 in a direction opposite to and greater than the sum of magnetic attractive force between the magnet 14 and the ferromagnetic ring 5, plus the hydrostatic force of urine against the valve element 8, the valve element 8 rotates, rolls, or slides to an arbitrary position within the valve housing 2, thus opening the valve seat assembly 36 for passage of fluid. The displaced (open check) position of the valve element 8 is determined by the approach direction of the switching magnet 15. The retaining ring 10 limits the movement of valve element 8 within the housing 2 such that at all possible displaced positions of the valve element the magnetic attraction between the valve element 8 and the ferromagnetic ring 5 is sufficient to return the valve element 8 to an aperture-occluding (closed check) position upon removal of the switching magnet 15. Thus, switching magnet 15 provides a source of magnetic force which can be selectively imposed on valve element 8 to control fluid discharge. Other non-bar or electromagnetic types of switching magnets may also be used, so long as such magnets can impart sufficient magnetic attractive force on the magnet 14 of the valve element 8 as it is brought in proximity of the valve element to move the valve element away from the valve seat assembly 36. The polarity shown in the figures for magnets 14 and 15 are for purposes of illustration, other polarity orientations may be used.

The axial thickness of the nonferromagnetic valve seat 4 (FIG. 1) determines the upper limit of attractive force between the spherical valve element 8 and ferromagnetic ring 5. This upper limit of attractive force may be decreased by increasing the thickness of the valve seat. Limiting this attractive force can facilitate the ability of the hand-held switching magnet 15 to impart force sufficient to open the valve under hydrostatic pressure.

Figure 3:
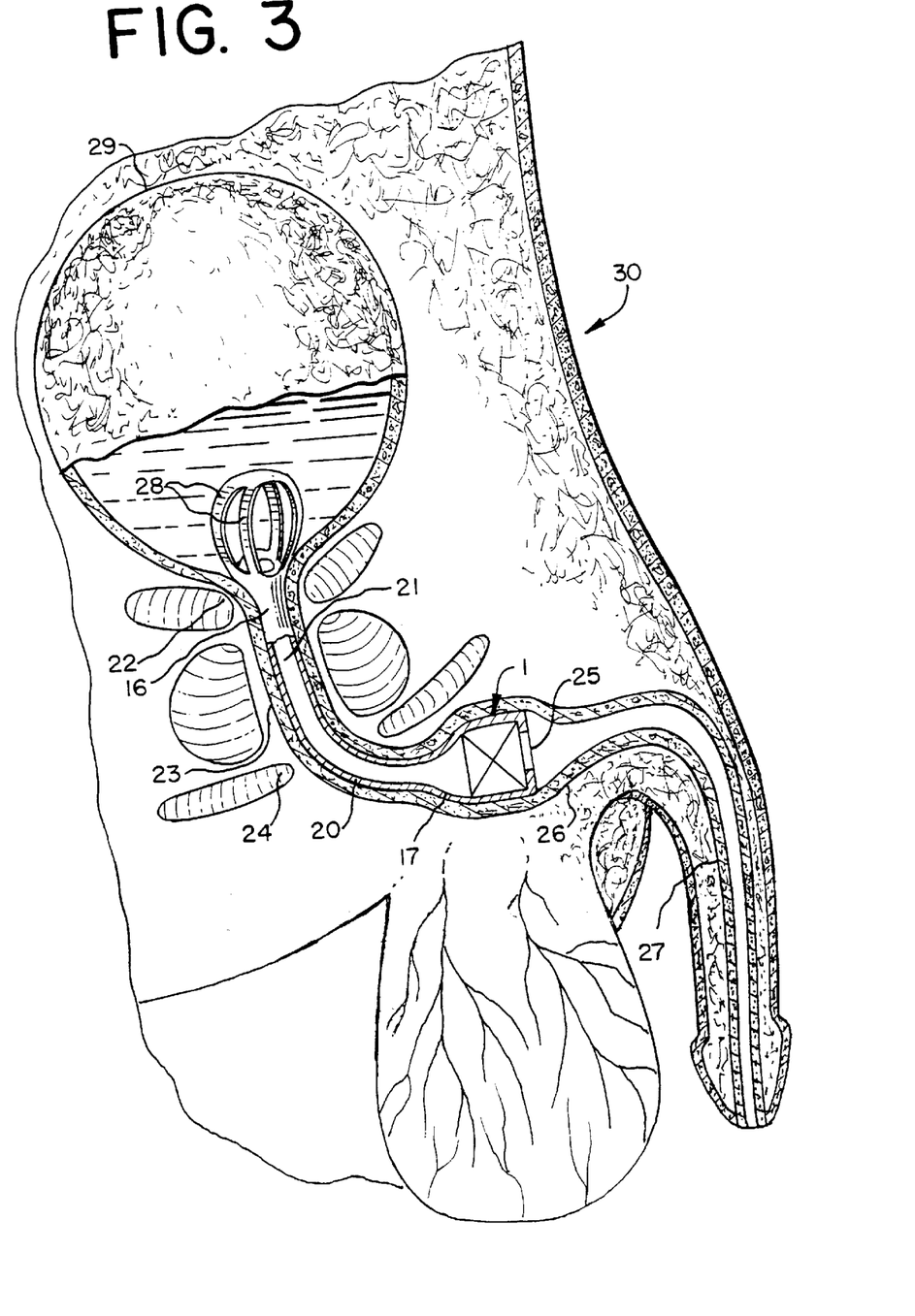
FIG. 3 is a sectional view of a portion of a human body showing the magnetic valve of the present invention implanted for controlling urine flow through the urethra.

Referring now to FIG. 3, a partial cross section of the human male abdomen 30 is schematically illustrated to show the positioning of the stent 16 and the valve assembly 1 within a patient. The abdomen 30 contains a bladder 29, bladder neck 22, prosthetic urethra 23, external sphincter 24, bulbous urethra 26, and pendulous urethra 27, which are defined here only for purposes of discussion. A lumen 21 of the tube 20 conducts urine from the bladder 29 through the bladder neck 22, prosthetic urethra 23, and external sphincter 24. The valve assembly 1 releases urine through outlet port 25 into a portion of the bulbous urethra 26 which, in turn, conducts it to the pendulous urethra 27 and out of the body. Collapsible loops 28 retain the stent 16 in the bladder 29 by contact against the normally closed bladder neck 22. The bulge 17 prevents migration of the stent into the bladder by impinging on the normally closed external sphincter 24. Bulge 17 further has flanges 40 shown in FIG. 4 in end view, taken along the section lines A—A of FIG. 2. The flanges 40 function as gripping points for insertion into and removal from the urethra of stent 16 which contains the valve assembly 1.

The valve assembly 1 is normally placed in the bulge 17 in an open-against-pressure orientation as shown in FIG. 2. However, the valve assembly 1 may be reversed in the bulge 17 to function as a high pressure relief valve for male patients unable to operate the hand-held switching magnet 15, such as quadriplegics. When so reversed in the urine fluid stream, the valve assembly 1 operates in an open-with-pressure orientation, such that the magnetic attractive force between valve element 8 and ring 5 is not sufficient to close the valve until fluid drag approaches zero, i.e., when the bladder is approximately empty. Thus, in this orientation the valve assembly 1 can provide bladder filling and voiding to men who wear urine collection devices, such as condom catheters.

Figures 4, 5:
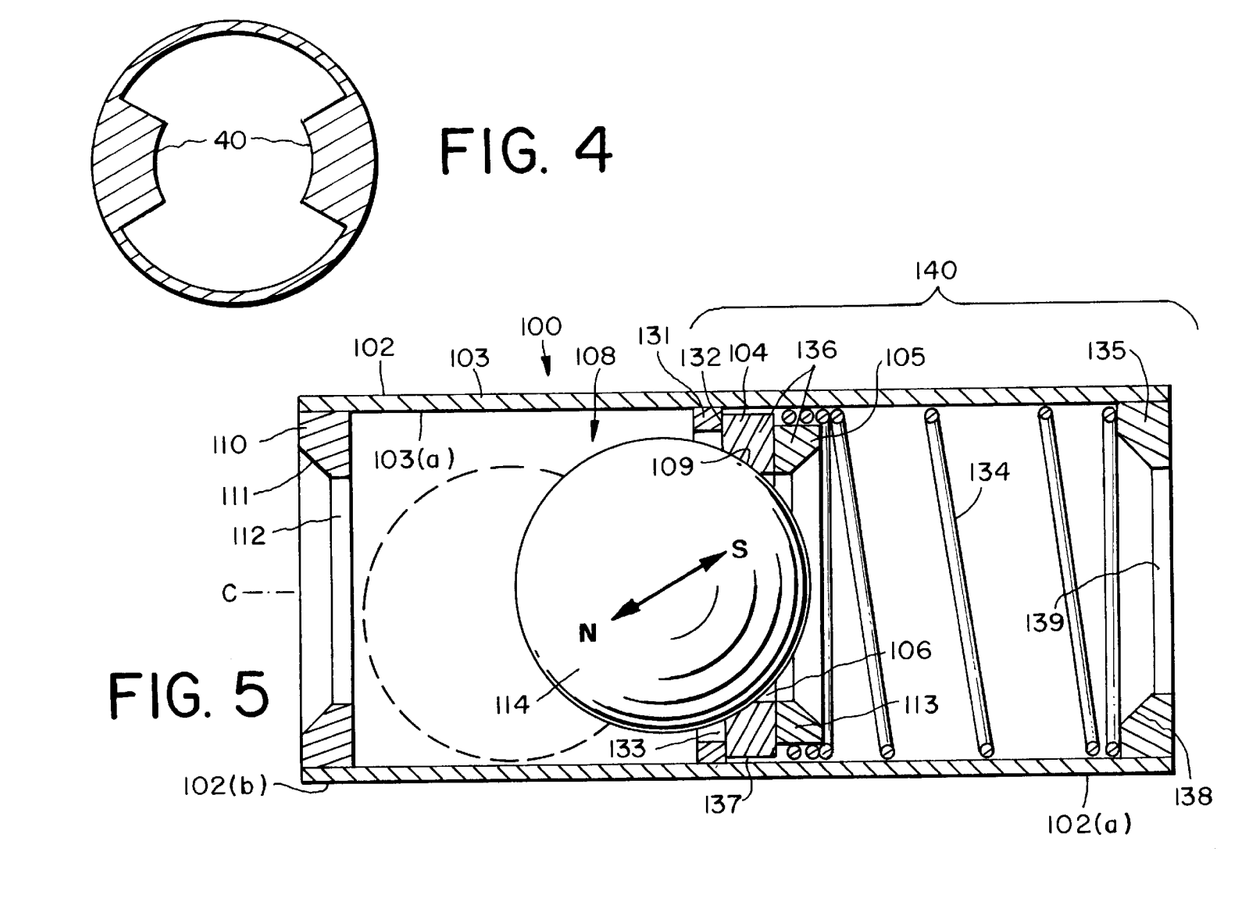
FIG. 4 is a section on lines A—A of FIG. 2.
FIG. 5 is a sectional view of the magnetic valve in accordance with the present invention with a mechanism for reducing hydrostatic pressure which may be excessive.

Referring now to FIG. 5, there is shown the magnetic valve of FIG. 1 with a mechanism 140 for relieving excessive hydrostatic pressure in which the valve seat assembly 36 (valve seat 4 and ring 5) is slidable axially in the housing 2, rather than attached to the housing. The magnetic valve with this mechanism 140 is denoted as 100 in FIG. 5. Corresponding numeral designations incremented by 100, refer to like parts or of parts performing like functions with respect to parts and their function described in connection with FIG. 1 and require no further detailed description. Under normal fluid pressure conditions, the valve assembly 100 functions in an identical manner as the valve assembly 1 of FIG. 1. The distinguishing aspect of the valve assembly 100 of FIG. 5 is an additional mechanism 140 for high pressure relief when conditions of excess hydrostatic pressure prevail in patients who experience uncontrolled bladder detrusor contractions or who are unaware of bladder filling due to nerve damage, coma, or other debilitating conditions. Mechanism 140 may also provide pressure relief for a gradual increase in fluid pressure, or fluid pressure spikes or surges (spontaneous increases in fluid pressure) which may be caused by sneezes, coughs, or other physical activity. The mechanism 140 exhibits little pressure relief hysterisis, releasing small quantities of urine during such fluid pressure spikes.

The mechanism 140 includes a nonferromagnetic annular flange 131 fixedly and sealingly attached against an inner bore 103(a) of tubular housing 102 having a continuous sidewall 103. The flange 131 has a planar sealing surface 132. The mechanism further includes a valve seat assembly 136 which is slidably disposed in a generally loose fit within the inner bore 103(a). The valve seat assembly 136 consists of a nonferromagnetic circular ring 104 which is bonded concentrically to a circular ferromagnetic attractive ring 105 of high magnetic permeability.

A planar sealing surface 133 of the ring 104 is held in tight sealing contact with the planar surface 132 by compression of a spring 134 of mechanism 140 which is retained within the housing 102 by a spring retainer ring 135. Retaining ring 135 has a conical face 138 and cylindrical aperture 139 concentric with the housing 102. Retaining ring 135 may be similar to retaining ring 110. The conical faces 111 and 138 of retaining rings 110 and 135, and conical face 113 of valve seat assembly 136 reduce fluid drag at respective cylindrical apertures 112, 139 and 106. The spherical magnet valve element 108 is normally attracted to ring 105 causing it to occlude the cylindrical aperture 106 of the valve seat 104 by continuous contact with face 109, which provides a sealing surface with the valve element 108. Mechanism 140 is located at end 102(a) of the housing which is similar to end 2(a) of valve assembly 1 (FIG. 1) extended to accommodate mechanism 140.

Figure 6:
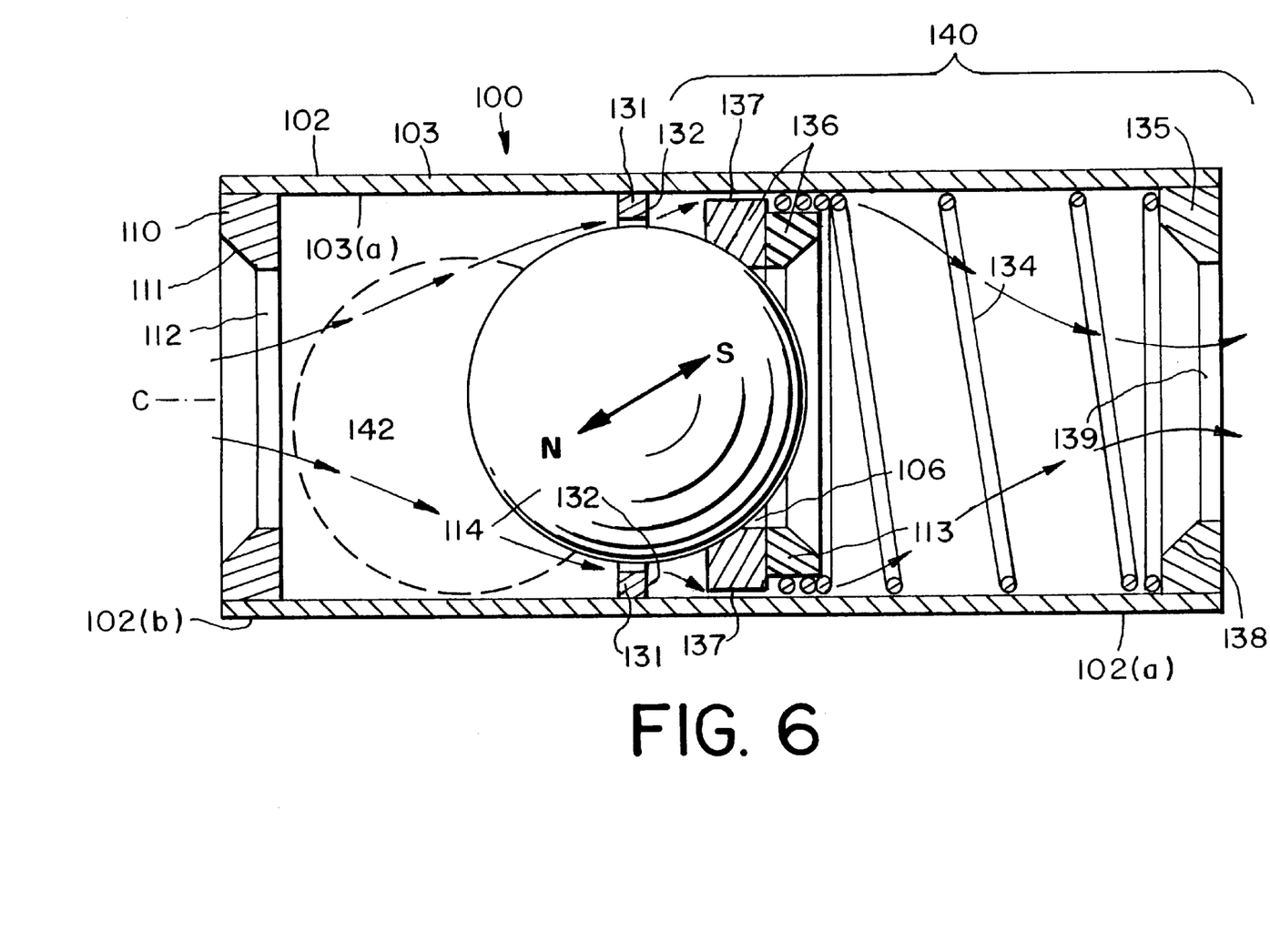
FIG. 6 is the same view as FIG. 5 showing an example of the operation of the mechanism for reducing hydrostatic pressure.

The valve assembly 100 is positioned within an intraprostatic stent catheter assembly like that shown in FIG. 2 and is then positioned within the bulbous urethra 26 as indicated in FIG. 3. Under normal conditions ring 104 of the valve seat assembly sealingly engages the surface 132 of flange 131, thereby enabling the magnetic valve 100 to function responsive to the proximity of the switching magnet 15 as described earlier in connection to FIGS. 1 and 2. However, under conditions of excess hydrostatic pressure, the valve element 108 and the valve seat assembly 136 are displaced together in the direction of the spring retaining ring 135, thereby compressing the spring 134, disengaging valve seat 104 from the surface 132 of flange 131, and opening a passage for urine flow at 137 surrounding the valve seat assembly 136 (i.e., valve seat 104 and ring 105). This, as shown, for example, in valve assembly 100 of FIG. 6, in which arrows 142 show the path of urine. Upon relief of the excess pressure condition, the valve seat assembly 136 is returned to sealing engagement (FIG. 5) against the planar sealing surface 132 by decompression of the spring 134. Hydrostatic pressure at which relief begins is determined by a prestress of the spring 134. The valve element 108 is sized to pass through the annular flange 131 without occluding urine flow through the flange 131. The spring constant of the spring 134 is chosen to prevent bottoming of the spring 134 against the retainer 135 at hydrostatic pressures experienced during uncontrolled bladder detrusor contractions, while allowing bottoming during higher pressure spikes induced by sneezes and coughs.

It will be apparent to those skilled in the art that the valve assemblies 1 and 100 of the present invention can be used in other environments not exclusive to the human body where reliable self-contained remotely actuated valves are required.

From the foregoing description, it will be apparent that there has been provided an improved intraurethral magnetic valve. Variations and modifications in the herein described system in accordance with the invention will undoubtedly suggest themselves to those skilled in the art. Accordingly, the foregoing description should be taken as illustrative and not in a limiting sense.

What is claimed is:

1. An intraurethral magnetic valve for insertion into the urethra of a person's body to selectively provide fluid discharge therefrom, comprising:
    a housing having a valve seat, a spherical permanent magnet valve element, and means for magnetically attracting said valve element through said valve seat which is noncontact with said valve element; and
    said valve element being disposed for universal movement in said housing, but normally in sealing engagement with said valve seat by magnetic attraction to said means, and being responsive to an external magnetic force to move from the valve seat thereby providing for fluid discharge via said housing, and said valve element returning to said valve seat upon removal of said external magnetic force.

2. The intraurethral magnetic valve of claim 1 wherein said magnetic attracting means is a ferromagnetic ring, said valve seat is nonmagnetic and part of a valve seat assembly, and said valve seat assembly further comprises said ferromagnetic ring, in which said valve element is normally in sealing engagement with said valve seat by magnetic attraction to said ferromagnetic ring through said valve seat.

3. The intraurethral magnetic valve of claim 2 wherein said valve seat has a thickness which limits the magnetic attraction between said valve element and said ferromagnetic ring.

4. The intraurethral magnetic valve of claim 2 wherein said valve seat assembly is sealingly attached within the housing.

5. The intraurethral magnetic valve of claim 2 further comprising a nonmagnetic retaining ring attached within the housing for retaining the valve element within the housing when fluid discharge is to be provided.

6. The intraurethral magnetic valve of claim 5 wherein the retaining ring restricts displacement of the magnetic valve element so that from all possible displacement positions sufficient magnetic attractive force exists between the valve element and the ferromagnetic ring to return the valve element to sealing engagement with the valve seat.

7. The intraurethral magnetic valve of claim 5 wherein the valve seat assembly and the retaining ring each have a cylindrical aperture concentric with the housing, the ferromagnetic ring and the retaining ring each have a conical face extending axially outwardly from the corresponding cylindrical aperture so as to reduce fluid drag during fluid discharge, and said valve seat has a face providing a sealing surface.

8. The intraurethral magnetic valve of claim 1 wherein said housing is cylindrical and nonmagnetic, and has a continuous sidewall.

9. The intraurethral magnetic valve of claim 5 wherein the spherical permanent magnet valve element is magnetized through an arbitrary center line thereof and is coated with a biocompatible material, the housing and valve seat and retaining ring are formed of a nonmagnetic biocompatible material, and the ferromagnetic ring is coated with a biocompatible material.

10. The intraurethral magnetic valve of claim 1 further comprising means for opening the valve comprising a source of said magnetic force in spaced relation to the person's body, and said source of magnetic force is selectively imposed on the valve element to control fluid discharge.

11. The intraurethral magnetic valve of claim 1 wherein the means for opening said magnetic valve comprises a switching magnet which is magnetized along a center line axis.

12. The intraurethral magnetic valve of claim 1 further comprising means for inserting the magnetic valve within the urethra of the person's body.

13. The intraurethral magnetic valve of claim 12 wherein the means for inserting the magnetic valve within the urethra of the person's body comprises a contoured placement catheter having an elongated tubular body member, rings for resiliently securing the catheter in the bladder, a bulge for holding the valve and for resiliently positioning and securing the catheter in the urethra, and flanges on the bulge for gripping the catheter during insertion and removal from the person's urethra.

14. The intraurethral magnetic valve of claim 1 where in said valve element is rotatable in said valve seat responsive to an external magnetic force to remove deposits on said valve element.

15. The intraurethral magnetic valve of claim 1 further comprising means in said housing for relieving excessive hydrostatic pressure in the bladder.

16. The intraurethral magnetic valve of claim 2 wherein the valve seat assembly is axially slidable within the housing, a compression spring having one end thereof in contact with the slidable valve seat assembly and another end in contact with a nonmagnetic spring retaining ring attached within the housing.

17. The intraurethral magnetic valve of claim 16 further comprising a nonmagnetic annular flange sealingly attached within the housing and having a planar sealing surface and an aperture sized to permit the spherical valve element to pass therethrough, the spring biasing the valve seat assembly into sealing engagement with the planar sealing surface of the flange, the valve element and the valve seat assembly being slidable together in an axial direction toward the spring so as to additionally provide controlled fluid discharge under conditions when pressure increases.

18. The intraurethral magnetic valve of claim 17 wherein the spring retaining ring has a cylindrical aperture concentric with the housing and a conical face extending axially inwardly from the cylindrical aperture, the spring retaining ring and the annular flange are formed of a biocompatible material, and the spring is coated with a biocompatible material.

19. The intraurethral magnetic valve of claim 1 further comprising means for enabling said housing to be located in the urethra in which said valve opens against fluid pressure in said urethra or said valve opens with fluid pressure in said urethra.

20. The intraurethral magnetic valve of claim 1 wherein said housing further comprises a nonmagnetic means for retaining the valve element within the housing when fluid discharge is to be provided.

21. An intraurethral magnetic valve for insertion into the urethra of a person's body to provide fluid discharge therefrom selectively under normal conditions and to provide controlled fluid discharge therefrom under conditions when fluid pressure increases, comprising in combination a tubular and nonmagnetic housing having a continuous sidewall and disposed within the housing an axially slidable valve seat assembly comprised of a ferromagnetic ring bonded to a nonmagnetic valve seat having a face thereof axially spaced from the ferromagnetic ring, a spherical permanent magnet valve element normally held in sealing engagement with the face of the valve seat by magnetic attraction therethrough to the ferromagnetic ring, a nonmagnetic annular flange sealingly attached within the housing and having a planar sealing surface which normally sealingly engages a planar sealing surface of the valve seat assembly, a nonmagnetic retaining ring attached within the housing for retaining the valve element within the housing, and a nonmagnetic spring retaining ring attached within the housing, and a compression spring disposed between the spring retaining ring and the valve seat assembly, the spring biasing the valve seat assembly into sealing engagement with the planar sealing surface of the flange, means for selectively opening the valve comprising a source of magnetic attraction in spaced relation to the person's body, the source of magnetic attraction selectively imposes a magnetic force on the valve element which moves the valve element away from the valve seat thereby providing the selective fluid discharge under normal conditions, and the valve element and the valve seat assembly being slidable together in an axial direction toward the spring so as to additionally provide controlled fluid discharge under conditions when fluid pressure increases.

22. The intraurethral magnetic valve of claim 21, wherein the spring retaining ring, the valve seat assembly, and the retaining ring each having a cylindrical aperture concentric with the housing, and each having a conical face extending from the corresponding cylindrical aperture so as to reduce fluid drag during fluid discharge, the face of the valve seat having a spherical sealing surface, and the annular flange having an aperture sized to permit the spherical valve element to pass therethrough without occluding fluid flow through the flange aperture.

23. The intraurethral magnetic valve of claim 21, wherein the spherical permanent magnet valve element is magnetized through an arbitrary center line thereof and is coated with a biocompatible material, the compression spring and the ferromagnetic ring are coated with a biocompatible material, and the tubular housing, the spring retaining ring, the valve seat, the annular flange, and the retaining ring are formed of a biocompatible material.

24. The intraurethral magnetic valve of claim 21, wherein the means for opening the magnetic valve comprises a permanent switching magnet which is magnetized along its center line axis.

25. The intraurethral magnetic valve of claim 21, wherein the means for inserting the magnetic valve within the urethra of the person's body comprises a contoured placement catheter having an elongated tubular body member, rings for resiliently securing the catheter in the bladder, a bulge for holding the valve and for resiliently positioning and securing the catheter in the urethra, and flanges on the bulge for gripping the catheter during insertion and removal from the person's urethra.

26. The intraurethral magnetic valve of claim 21, wherein the compression spring is prestressed to hold the planar sealing surface of the valve seat assembly in sealing contact against the planar sealing surface of the annular flange, the spring being further compressed by excess pressure causing the valve seat assembly to be displaced from the annular flange thereby opening a passage for fluid flow between the valve seat assembly and the flange.

27. The intraurethral magnetic valve of claim 26, wherein said spring has a spring constant selected to limit displacement of the valve element and the valve seat assembly when exposed to hydrostatic pressure associated with bladder detrusor contractions, but not limit displacement when exposed to hydrostatic pressure spikes associated with sneezes, coughs, or physical activity.

28. The intraurethral magnetic valve of claim 21, wherein the retaining ring restricts displacement of the magnetic valve element so that from all possible displacement positions sufficient magnetic attractive force exists between the valve element and the ferromagnetic ring to return the valve element to sealing engagement with the valve seat.

29. A magnetic valve comprising in combination a tubular and nonmagnetic housing having a continuous sidewall and disposed within the housing, in sequence from one end thereof, a valve seat assembly comprised of a ferromagnetic ring and a nonmagnetic valve seat having a face thereof axially spaced from the ferromagnetic ring, the valve seat assembly sealingly attached within the housing, a spherical permanent magnet valve element held in sealing engagement with the face of the valve seat by magnetic attraction therethrough to the ferromagnetic ring, and a nonmagnetic retaining ring attached within the housing for retaining the valve element within the housing, means for opening the valve by a source of magnetic attraction positioned in spaced relation thereto, the source of the magnetic attraction selectively imposes a magnetic force on the valve element which rotates the valve element away from the valve seat, thereby opening a passage through the magnetic valve.

30. An intraurethral magnetic valve assembly for insertion into the urethra of a person's body to selectively provide fluid discharge therefrom, comprising:

a housing having a spherical permanent magnet valve element and a valve seat having means magnetically attractive to said valve element, in which said valve element is normally in sealing engagement with said valve seat, and is responsive to external magnetic force to move from the valve seat thereby providing for fluid discharge via said housing; and said housing further comprises non-magnetic means for restricting displacement of the valve element within said housing so that from all possible displacement positions sufficient magnetic attractive force exists between the valve element and the valve seat to return the valve element to sealing engagement with the valve seat when the external magnetic force is removed.

31. The intraurethral magnetic valve assembly according to claim 30 further comprising a catheter having said housing locatable in the urethra, wherein said catheter comprises a tube having a first end and a second end, in which said first end of the tube is located in the bladder of the body, and said second end of the tube has an outlet port adjacent said housing.

32. The intraurethral magnetic valve assembly according to claim 31 wherein said catheter further comprises a section coupled to said outlet port which contains said housing.

33. An intraurethral magnetic valve assembly for insertion into the urethra of a person's body to selectively provide fluid discharge therefrom, comprising:

a housing having a spherical permanent magnet valve element and a valve seat having means magnetically attractive to said valve element, in which said valve element is normally in sealing engagement with said valve seat, and is responsive to hydrostatic pressure able to move the valve element from the valve seat thereby providing for fluid discharge via said housing; and said housing further comprises nonmagnetic means for restricting displacement of the valve element within said housing so that from all possible displacement positions sufficient magnetic attractive force exists between the valve element and the valve seat to return the valve element to sealing engagement with the valve seat when the hydrostatic pressure is removed.

* * * * *